United States Patent
Sivadas

(10) Patent No.: US 11,224,540 B2
(45) Date of Patent: Jan. 18, 2022

(54) RADIALLY REPULSIVE MAGNETIC BEARING FOR SELF-ALIGNING ELEMENTS OF COUPLED PLATFORMS

(71) Applicant: Alcon Inc., Fribourg (CH)

(72) Inventor: Kulangara Sivadas, Foothill Ranch, CA (US)

(73) Assignee: Alcon Inc., Fribourg (CH)

( * ) Notice: Subject to any disclaimer, the term of this patent is extended or adjusted under 35 U.S.C. 154(b) by 124 days.

(21) Appl. No.: 16/516,374

(22) Filed: Jul. 19, 2019

(65) Prior Publication Data

US 2020/0022839 A1 Jan. 23, 2020

Related U.S. Application Data

(60) Provisional application No. 62/700,492, filed on Jul. 19, 2018.

(51) Int. Cl.
*F16C 32/04* (2006.01)
*A61F 9/008* (2006.01)
*A61B 17/00* (2006.01)
*A61B 18/20* (2006.01)

(52) U.S. Cl.
CPC .......... *A61F 9/008* (2013.01); *F16C 32/0402* (2013.01); *F16C 32/048* (2013.01); *F16C 32/0425* (2013.01); *A61B 2017/00526* (2013.01); *A61B 2017/00876* (2013.01); *A61B 2018/202* (2013.01); *A61F 9/00825* (2013.01); *A61F 2009/00874* (2013.01); *F16C 2316/10* (2013.01)

(58) Field of Classification Search
CPC ................ A61F 9/008; H01R 13/6205; A61B 2017/0046; A61B 2017/00526; A61B 2017/00876
See application file for complete search history.

(56) References Cited

U.S. PATENT DOCUMENTS

| | | | |
|---|---|---|---|
| 4,189,206 A | 2/1980 | Terai et al. | |
| 5,147,348 A * | 9/1992 | Leckrone | A61B 18/245 385/90 |
| 5,808,839 A | 9/1998 | Dunfield | |
| 6,102,582 A | 8/2000 | Espindola | |
| 7,618,177 B2 | 11/2009 | Cazzini | |
| 8,480,279 B2 | 7/2013 | Papac et al. | |
| 8,485,972 B2 | 7/2013 | Papac et al. | |
| 9,028,153 B2 | 5/2015 | Angelov | |

(Continued)

FOREIGN PATENT DOCUMENTS

| | | |
|---|---|---|
| CN | 1651780 A | 8/2005 |
| GB | 2066380 A | 7/1981 |

(Continued)

*Primary Examiner* — Allen Porter

(57) ABSTRACT

In certain embodiments, apparatus for self-aligning elements of coupled platforms includes a radially repulsive magnetic bearing. The radially repulsive magnetic bearing includes a first axially polarized magnet and a second axially polarized magnet that is concentrically disposed around the first axially polarized magnet and radially repulsive to the first axially polarized magnet. The radially repulsive magnetic bearing is configured to align a first element of a first platform with a second element of a second platform when the first and second platforms are coupled together.

7 Claims, 8 Drawing Sheets

(56) References Cited

U.S. PATENT DOCUMENTS

| | | | |
|---|---|---|---|
| 9,468,368 B2 | 10/2016 | Smith | |
| 9,486,360 B2 | 11/2016 | Chon | |
| 9,572,629 B1 | 2/2017 | Papac | |
| 9,655,524 B2 | 5/2017 | Wheatley | |
| 9,668,645 B2 | 6/2017 | Wheatley | |
| 9,782,063 B2 | 10/2017 | Bacher | |
| 9,910,338 B2 | 3/2018 | Smith | |
| 9,974,689 B2 | 5/2018 | Mcdonell | |
| 10,188,481 B2 | 1/2019 | Ulinskas | |
| 10,251,782 B2 | 4/2019 | Farley | |
| 2002/0018113 A1 | 2/2002 | Koh | |
| 2008/0027418 A1 | 1/2008 | Berry | |
| 2008/0188881 A1 | 8/2008 | Chon | |
| 2009/0131922 A1* | 5/2009 | Dewey | A61B 18/203 606/9 |
| 2011/0001379 A1 | 1/2011 | Mccarthy | |
| 2015/0063746 A1* | 3/2015 | Usui | G02B 6/421 385/14 |
| 2015/0133901 A1 | 5/2015 | Serdarevic | |
| 2016/0120697 A1 | 5/2016 | Farley | |
| 2018/0243137 A1 | 8/2018 | Diao | |
| 2018/0369016 A1 | 12/2018 | Underwood | |

FOREIGN PATENT DOCUMENTS

| | | | |
|---|---|---|---|
| JP | 2002081445 A | 3/2002 | |
| WO | WO2013062740 A1 | 5/2013 | |

* cited by examiner

RADIALLY REPULSIVE MAGNETIC BEARING FOR SELF-ALIGNING ELEMENTS OF COUPLED PLATFORMS

TECHNICAL FIELD

The present disclosure relates to radially repulsive magnetic bearings for self-aligning elements of coupled platforms, such as, for example, optical elements.

BACKGROUND OF THE INVENTION

Certain systems may require maintaining alignment between two elements (e.g., optical elements, electromagnetic elements, fluidic path elements). Drift may be introduced in one or both elements by thermal, structural, or other variations in the elements or the housings of the elements, causing misalignment between the elements. Current systems for maintaining alignment between two elements, such as optical elements, may include active, servo-based control mechanisms that utilize position sensors and micro-actuators. Such systems, however, may require complex and expensive electronic components, tuning of servo channels, a continuous power supply, and/or calibration/maintenance. Such systems may thus have lower reliability due to the many components involved, and may see performance degradation caused by head dissipation by the constituent components. Current systems may also comprise passive mechanisms that force the elements into alignment by virtue of having precisely controlled shapes such as cylindrical ferrules, alignment sleeves, and V-grooves. These systems, however, may experience non-repeatable alignment forces between insertions (de-mating/mating operations) caused by variations in contact conditions between the multiple surfaces involved.

SUMMARY OF THE INVENTION

In certain embodiments, apparatus for self-aligning elements of coupled platforms includes a radially repulsive magnetic bearing. The radially repulsive magnetic bearing includes a first axially polarized magnet and a second axially polarized magnet that is concentrically disposed around the first axially polarized magnet and radially repulsive to the first axially polarized magnet. The radially repulsive magnetic bearing is configured to align a first element of a first platform with a second element of a second platform when the first and second platforms are coupled together. In certain embodiments, the first and second axially polarized magnets may be mounted on the same platform (e.g., either the first platform or the second platform). In other embodiments, the first and second axially polarized magnets may be mounted on separate platforms (e.g., the first axially polarized magnet on the first platform and the second axially polarized magnet on the second platform).

In certain embodiments, an ophthalmic surgical system includes a laser source configured to generate optical pulses and direct the optical pulses along an optical path defined by one or more optical elements, and a housing configured to be coupled to a handpiece. The housing includes a radially repulsive magnetic bearing, which includes a first axially polarized magnet coupled to at least one of the optical elements and a second axially polarized magnet. The second axially polarized magnet is concentric with and radially repulsive to the first axially polarized magnet, and is coupled to the housing. The radially repulsive magnetic bearing is configured, when the housing is coupled to the handpiece, to optically align an optical element of the handpiece with the at least one optical element coupled to the first axially polarized magnet.

In certain embodiments, a method of manufacturing an assembly including a radially repulsive magnetic bearing includes forming first and second rings of unmagnetized magnetic material. The rings are generally annular-shaped and the first ring has an outer radius that is less than an inner radius of the second ring. The method also includes positioning the first ring within the second ring such that the first and second rings are concentric with one another and separated by a first shim, and positioning a thrust bearing, the first ring, and second ring within a cavity defined by a housing such that the thrust bearing is disposed at a first end of the housing opposite an opening defined by the housing, the thrust bearing is separated from a wall of the cavity by a second shim, and the first ring is separated from a portion of the housing by a third shim. The method further includes applying a magnetic field in an axial direction of the first and second rings, and removing the first, second, and third shims from the assembly.

Certain embodiments may provide one or more technical advantages, in some instances. As an example, aspects of the present disclosure may allow for elements of coupled platforms (e.g., optical elements, electromagnetic elements, or fluidic paths) to maintain alignment, even in the event of drift in a transverse direction by one of the elements (e.g., drift caused by thermal expansion in the platform, structural variations, or external forces). Thus, in embodiments where two optical elements (e.g., optical fibers, lenses, mirrors) are aligned, a high degree of optical coupling may be maintained between the two optical elements. Furthermore, aspects of the present disclosure may be implemented using readily-available, passive means (e.g., permanent magnets), without requiring electronics to be tuned, maintained, or temperature-controlled, which may translate to lower cost and higher reliability.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

Figure 1:
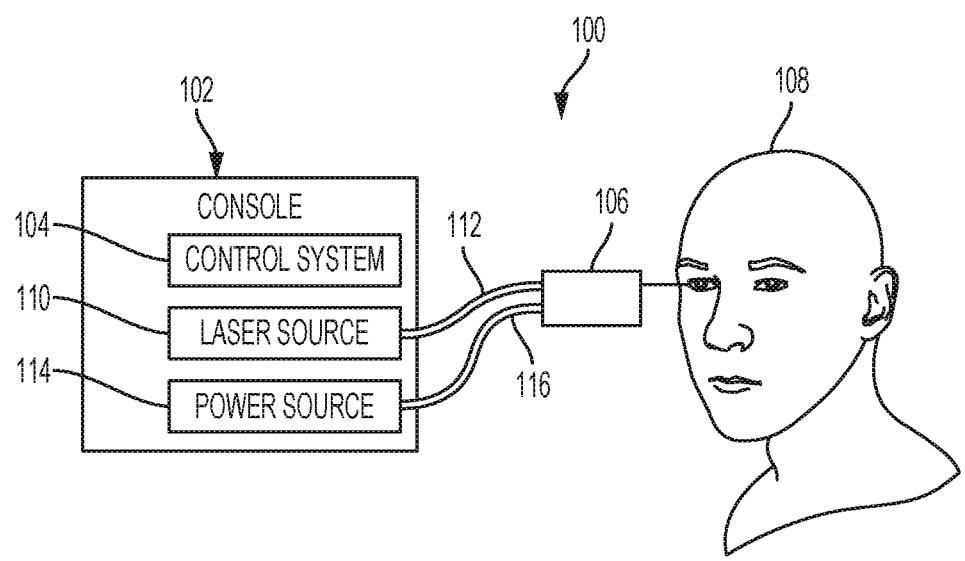
FIG. 1 is a diagram of an example ophthalmic surgical system with an attached handpiece for performing a surgical procedure on a patient.

One skilled in the art will understand that the drawings, described below, are for illustration purposes only, and are not intended to limit the scope of applicant's disclosure.

DETAILED DESCRIPTION OF THE INVENTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Alterations and further modifications to the described systems, devices, and methods, and any further application of the principles of the present disclosure are contemplated as would normally occur to one skilled in the art to which the disclosure relates. In particular, it is contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

FIG. 1 is a diagram of an example ophthalmic surgical system 100 with an attached handpiece 106 for performing a surgical procedure on a patient 108. The ophthalmic surgical system 100 includes a console 102 with a control system 104, a laser source 110, and a power source 114. The console 102 is coupled to a handpiece 106, which may include a surgical probe for performing the surgical procedure on the patient 108. The handpiece 106 is coupled to the console via an optical cable 112, which is coupled to the laser source 110 of the console 102, and a cable 116, which is coupled to the power source of the console 102. The handpiece 106 may be coupled to the console 102 in another manner, which may depend on the type of console 102, type of handpiece 106, or both. In the example shown, the ophthalmic surgical system 100 is configured to perform a photodisruption-based vitrectomy procedure on an eye of the patient 108 using the handpiece 106. However, the ophthalmic surgical system 100 may be configured to perform other ophthalmic surgical procedures using the laser source 110. The ophthalmic surgical system 100 may include additional or fewer components and features than those illustrated in FIG. 1.

The example control system 104 controls operation of the various components of the console 102. For example, in some instances, the control system 104 controls operation of the laser source 110, such as generation of optical pulses sent to the handpiece 106 for performing the surgical procedure on the patient 108. The control system 104 may include a processor, a memory, and other hardware to control the various components of the console 102 or the handpiece 106.

The example laser source 110 generates optical signals for transmission to the handpiece 106 to perform the surgical procedure. The laser source 110 may include a femtosecond laser, or another type of laser. In some cases, the optical signals generated by the laser source 110 are configured to cause photodisruption within an eye of the patient 108. The laser source 110 communicates the optical signals to the handpiece 106 through the optical cable 112. The optical cable 112 includes a waveguide that is designed to effectively propagate the optical signals from the laser source 110 to the handpiece 106.

The example power source 114 is used to provide power to the handpiece 106. Various types of power sources may be included in the power source 114. For example, if the handpiece 106 requires electrical powered, the power source 114 may include an electrical power source such as a battery or voltage supply to provide an appropriate voltage or current. In such a case, the cable 116 would include a power cable. As another example, if the handpiece 106 requires pneumatic power, then the power source 114 may include a compressed fluid supply. In such a case, the cable 116 would include a pneumatic tube connecting the compressed fluid supply to the handpiece 106.

Other connections between the handpiece 106 and the console 102 may be used as well. For example, the console may include a suction or aspiration mechanism that connects with an aspiration lumen on the handpiece 106. While the optical cable 112 and the cable 116 are illustrated separately in FIG. 1, in some cases, all connections between the console 102 and the handpiece 106 may be within a single cable.

Figure 2:
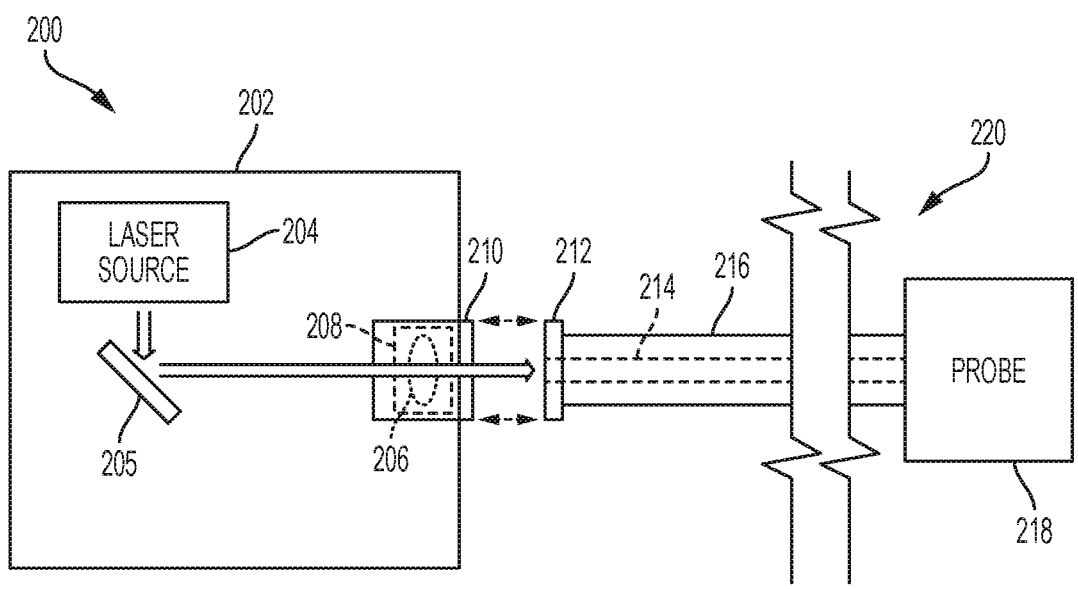
FIG. 2 is a diagram showing an example system for connecting an ophthalmic surgical system and a handpiece.

FIG. 2 is a diagram showing an example system 200 for connecting a console 202 of an ophthalmic surgical system (e.g., the ophthalmic surgical system 100 of FIG. 1) and a handpiece 220. In the example shown, the console 202 includes a laser source 204, a mirror 205, a lens 206, a radially repulsive magnetic bearing 208, and a housing 210 for coupling the console 202 to the handpiece 220. The console 202 and the laser source 204 may be implemented similar to the console 102 and laser source 110 of FIG. 1, respectively. The handpiece 220 includes a connector 212 attached to an optical cable 216 (which includes an optical waveguide 214) that extends to a surgical probe 218 of the handpiece 220.

The handpiece 220 is configured to couple to the housing 210 of the console 202 via the connector 212. The connector 212 and housing 210 may be configured to couple together using a fastener using any suitable means, such as, for example, a threaded connection fastener, a magnetic connection fastener, a quick-release connection fastener, or another type of connection mechanism. The connector 212 is coupled to an optical cable 216 that includes a waveguide 214 for transmitting optical signals generated by the laser source 204 to the handpiece 220.

As shown in FIG. 2, the laser source 204, mirror 205, and lens 206 form an optical path within the console 202. That is, optical signals (e.g., optical pulses) generated by the laser source 204 may be directed toward the mirror 205, which may be arranged such that it reflects the optical signals from the laser source 204 toward the lens 206. The optical path may include additional, fewer, or different optical elements than those shown in FIG. 2. For example, the mirror 205 may direct optical signals into a lens (other than the lens 206), which may further direct the optical signals into an optical fiber disposed within the radially repulsive magnetic bearing (e.g., the optical fiber 304 of FIGS. 3A-3B).

When the housing 210 and connector 212 are coupled together, the radially repulsive magnetic bearing 208 may allow for alignment of the optical elements of the two platforms (e.g., the console 202 and the handpiece 220). That is, the radially repulsive magnetic bearing 208 may serve to self-align the waveguide 214 of the optical cable 216 with the optical path created by the laser source 204, mirror 205, and lens 206. The radially repulsive magnetic bearing 208 may be implemented similar to the radially repulsive magnetic bearing 208 of FIGS. 3A-3B, or in another manner. For instance, the radially repulsive magnetic bearing 208 may include two concentric and radially repulsive magnets (permanent or electromagnetic) that serve to align the waveguide 214 with the optical path in the console 202.

The example system 200 may include additional, fewer, or other components than those illustrated in FIG. 2. For example, although FIG. 2 shows a radially repulsive magnetic bearing 208 in the housing 210 for aligning the waveguide 214 of the optical cable 216 with the optical path created by the mirror 205 and lens 206, additional or other radially repulsive magnetic bearings may be utilized to align other elements of the system 200, such as to align the mirror 205 and the lens 206.

Figure 3A:
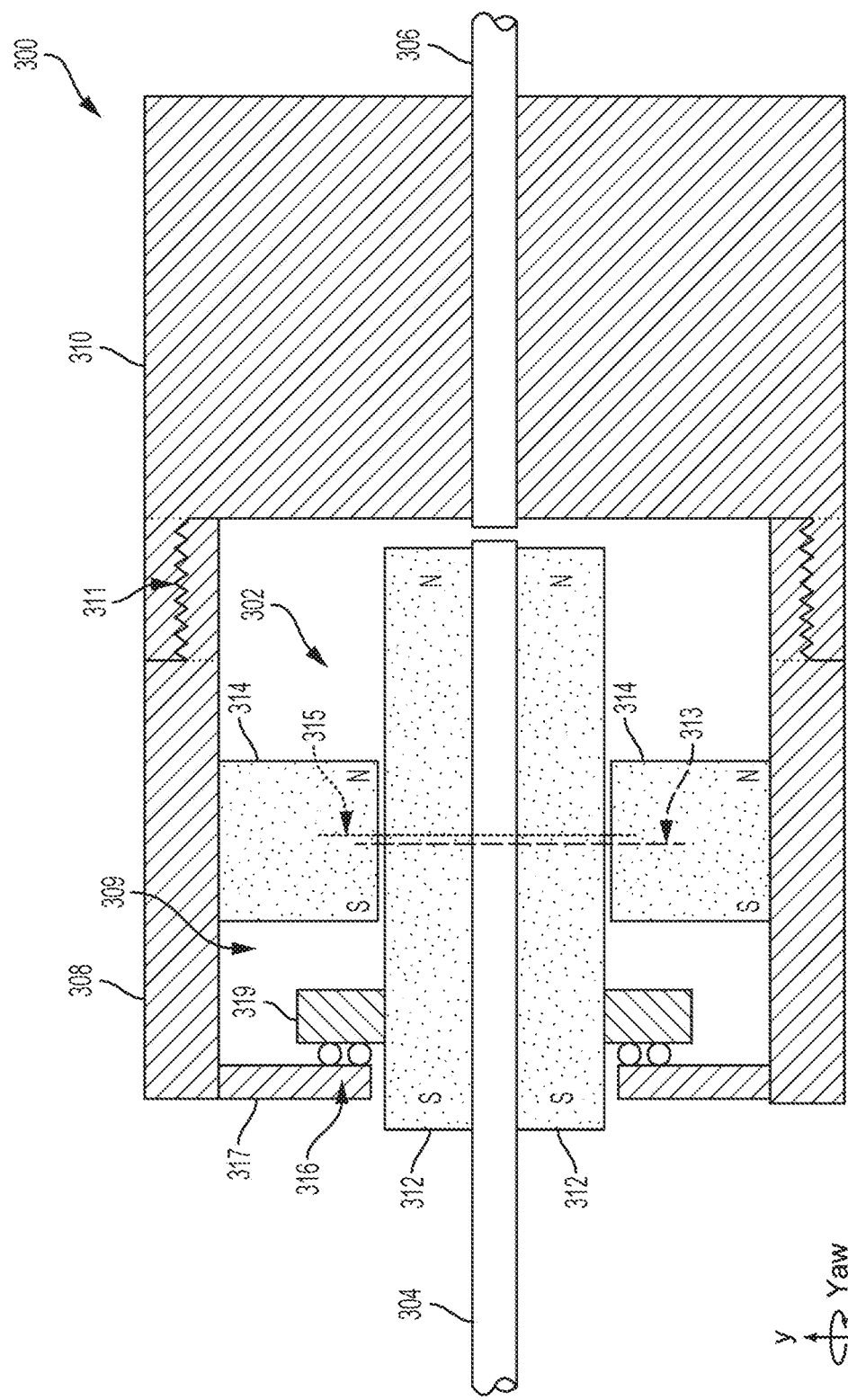
FIG. 3A is a cross-sectional view of an example system for self-aligning elements of two platforms using a radially repulsive magnetic bearing.
Figure 3B:
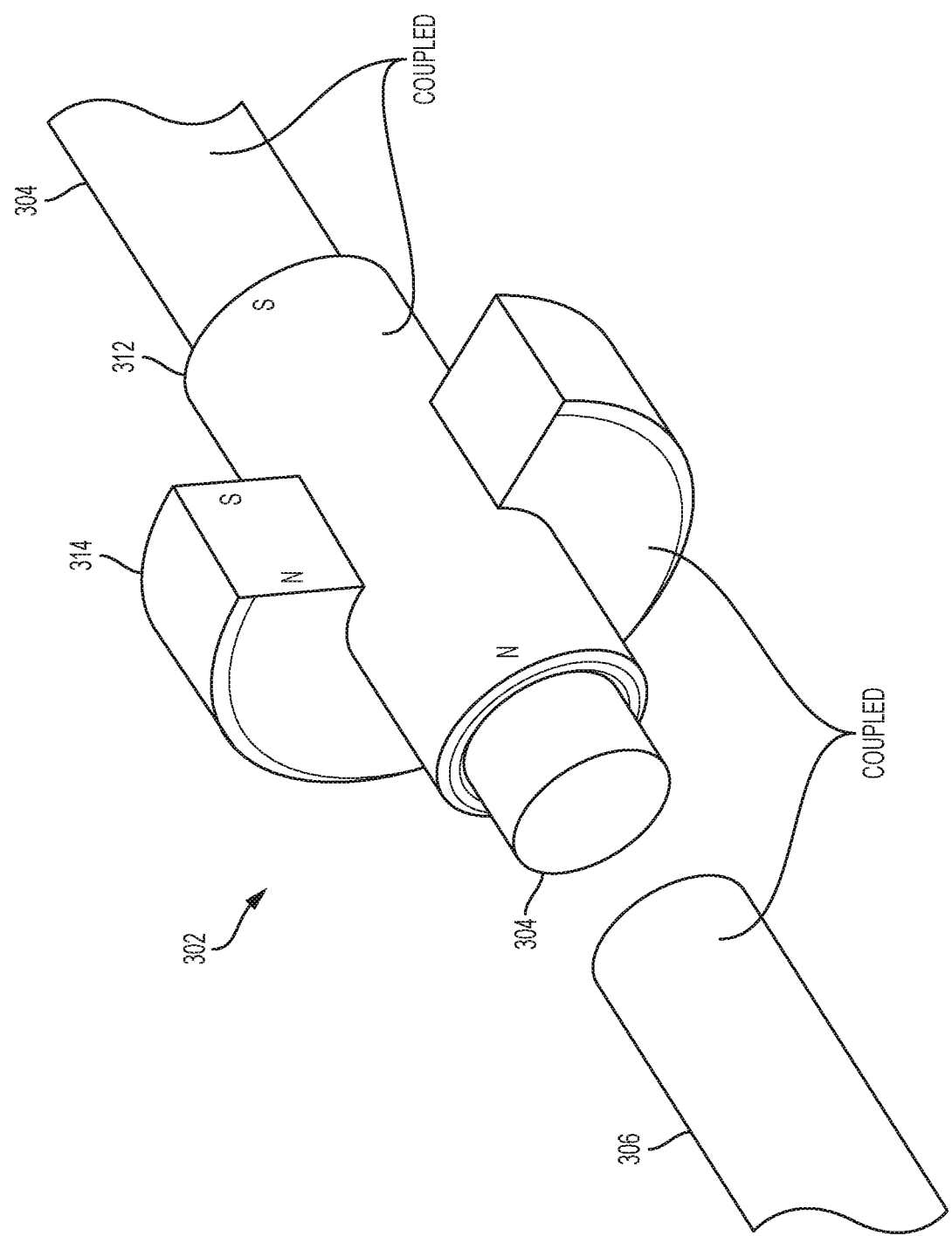
FIG. 3B is a perspective view of the example system illustrated in FIG. 3A

FIGS. 3A-3B are diagrams of an example system 300 for self-aligning elements of two platforms using a radially repulsive magnetic bearing. In particular, FIG. 3A shows a cross-sectional view of the example system 300, while FIG. 3B shows a perspective view of the example radially repulsive magnetic bearing 302 of the example system 300. The example system 300 may be used to radially self-align elements of two coupled platforms. In some cases, for example, the elements may be optical elements (e.g., optical fibers as shown in FIGS. 3A-3B, or other types of optical elements, such as lenses, mirrors, prisms, diffraction gratings, etc.), electromagnetic waveguides (e.g., microwave waveguides), acoustic waveguides, fluidic path elements, or other types of elements. In many instances, radially repulsive magnetic bearings may be unstable along the longitudinal axis. However, the system 300 provides a longitudinally-stable magnetic bearing 302 that self-aligns elements of coupled platforms in the radial direction. This magnetic bearing also imparts significant torsional rigidity, and therefore stability, to the platforms along axes orthogonal to the longitudinal axis In the example shown, the system 300 includes a radially repulsive magnetic bearing 302 that aligns the optical fibers 304, 306. The optical fiber 304 is a component of, or coupled to, a first platform (e.g., the console 202 of FIG. 2) and the optical fiber 306 is a component of, or coupled to a second platform (e.g., the handpiece 220 of FIG. 2). Examples of optical fiber 304 and/or optical fiber 306 may each comprise a single-core fiber, a multi-core fiber, or a plurality of optical fibers. The radially repulsive magnetic bearing 302 is positioned within a cavity 309 defined by a housing 308 of a first platform (e.g., the housing 210 of FIG. 2). The housing 308 is coupled to a connector 310 of a second platform (e.g., the connector 212 of FIG. 2) via a threaded fastener 311, bayonet mount, or snap cap fitting.

The radially repulsive magnetic bearing 302 includes a first axially polarized magnet 312 and a second axially polarized magnet 314 disposed around the first axially polarized magnet 312. In FIG. 3A, the axial direction may refer to the left-to-right direction. The first axially polarized magnet 312 and a second axially polarized magnet 314 are positioned such that a gap remains between the magnets 312, 314. The second axially polarized magnet 314 is concentric with and radially repulsive to the first axially polarized magnet 312 so that the optical fiber 304 is aligned with the optical fiber 306 when the first and second platforms are coupled together as shown. In the example shown, the second axially polarized magnet 314 is coupled to a wall of the cavity 309, so that the magnet 314 is coupled (via the threaded fastener 311) to the connector 310 when the housing 308 and connector 310 are coupled together. In the example shown, the optical fiber 304 is disposed within (e.g., coupled to an interior portion of) the first axially polarized magnet 312 and the optical fiber 306 is disposed within (e.g., coupled to an interior portion of) the connector 310. The axially polarized magnets 312 may be implemented using permanent magnets, such as neodymium magnets (e.g., NdFeB magnets), electromagnets, other types of magnets, or a combination thereof.

In the example shown, the axial length of the first axially polarized magnet 312 is greater than an axial length of the second axially polarized magnet 314. However, in particular embodiments, the first axially polarized magnet may have an axial length less than or equal to an axial length of the second axially polarized magnet. As shown in FIG. 3B, the magnets 312, 314 are generally annular-shaped; however, the magnets may be formed in another manner. In addition, as shown in FIG. 3A, the magnetic neutral axis 315 of the magnets 312, 314 is offset from the structural symmetrical axis 313 of the first axially polarized magnet 312. The offset between the magnets 312, 314 causes a force in the first axially polarized magnet 312, which is counteracted by a thrust bearing 316 coupled to the first axially polarized magnet 312, creating axial stability in the radially repulsive magnetic bearing 302. While the thrust bearing 316 is primarily configured to allow movement of the first axially polarized magnet 312 in directions orthogonal to the longitudinal axis of the magnets 312, 314, it also provides limited compliance about the pitch and yaw axes against undesirable rotational moments. The thrust bearing 316 may be implemented using one or more of a roller bearing (e.g., as shown in FIG. 3A), a fluid bearing, a film bearing, a flexure bearing, or a magnetic bearing. In the example shown, the thrust bearing 316 is a roller bearing disposed, at a first end of the housing 308 opposite the end of the housing that includes the threaded fastener 311, between a portion 317 of the housing 308 and an attachment 319 to the first axially polarized magnet 312.

As shown in FIG. 3A, when the housing 308 and connector 310 are coupled together, the optical fibers 304, 306 are aligned with a small gap between the fibers. The gap may be defined by the thrust bearing 316, the threaded fastener 311, or a combination thereof. That is, the size of such components may determine the gap left between the optical fibers 304, 306 when the two platforms are coupled together. In the event of drift in either of the platforms (which may be due to thermal expansion or contraction, structural variations or movements in the platforms, or other reasons), the optical fibers 304, 306 may remain aligned due to the radially repulsive magnetic bearing 302. Thus, the radially repulsive magnetic bearing 302 may be said to self-align the optical fibers 304, 306.

For example, if the housing 308, the connector 310, or both were to drift (e.g., expand from thermal variations), the magnet 314 would move along with the drift since it is coupled to both the housing 308 and connector 310. The drift in either platform would accordingly cause the optical fiber 306 to move along with the drift movement. However, because of radial compliance provided by thrust bearing 319, the magnet 312 may move along with the drift pulled by the change in the magnetic forces between the magnets 312, 314 caused by the drift. This allows the optical fiber 304 to self-align with the optical fiber 306 in the presence of any drift.

The example system 300 may include additional, fewer, or other components than those illustrated in FIGS. 3A-3B. In addition, the radially repulsive magnetic bearing 302 may be used to align other types of elements than those shown in FIGS. 3A-3B. For example, although FIGS. 3A-3B show a radially repulsive magnetic bearing 302 aligning optical fibers 304, 306, the radially repulsive magnetic bearing 302 may be used to align other types of elements as well.

Figure 4A:
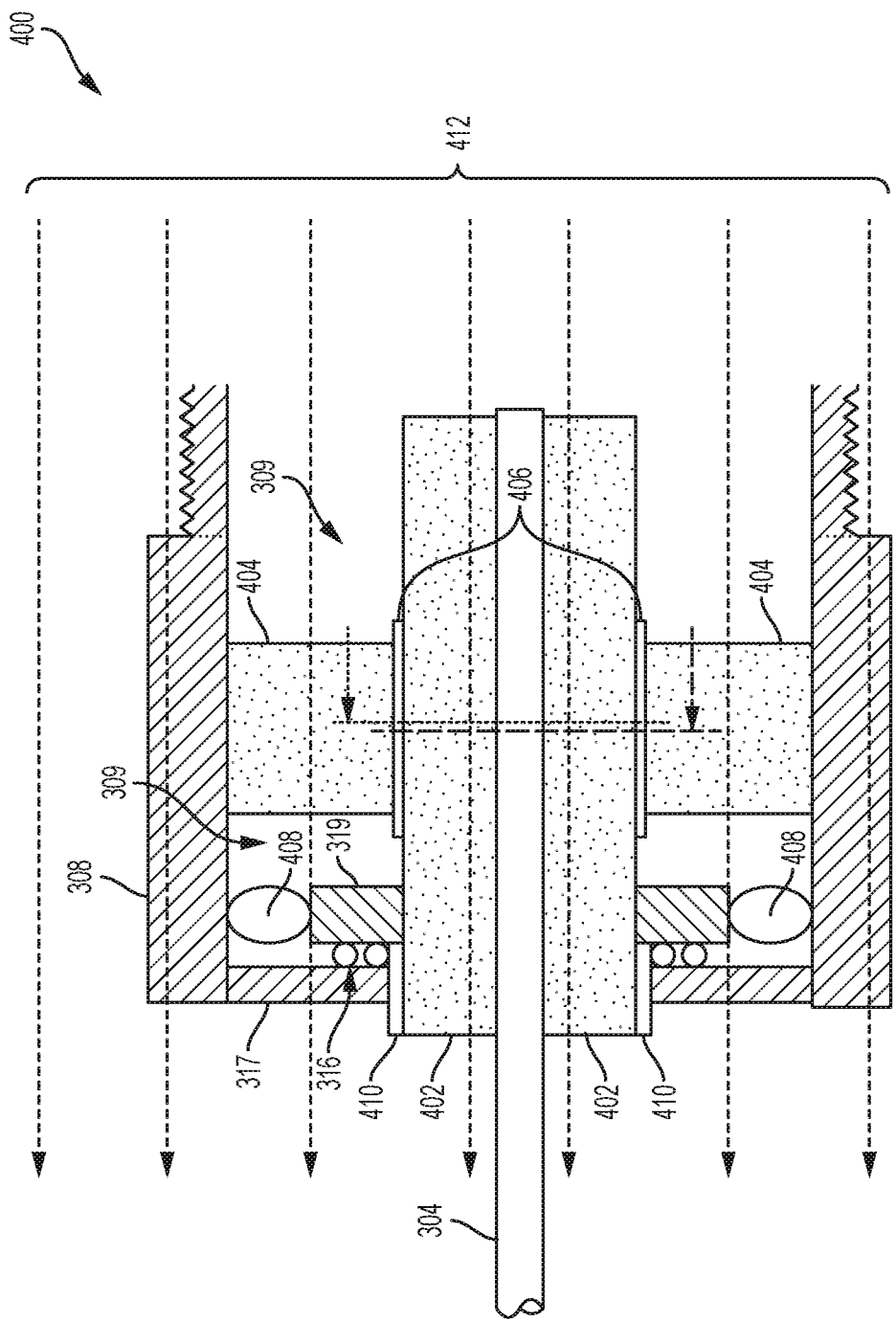
FIGS. 4A and 4B are diagrams showing an example process for manufacturing the assembly that includes a radially repulsive magnetic bearing shown in FIGS. 3A and 3B.
Figure 4B:
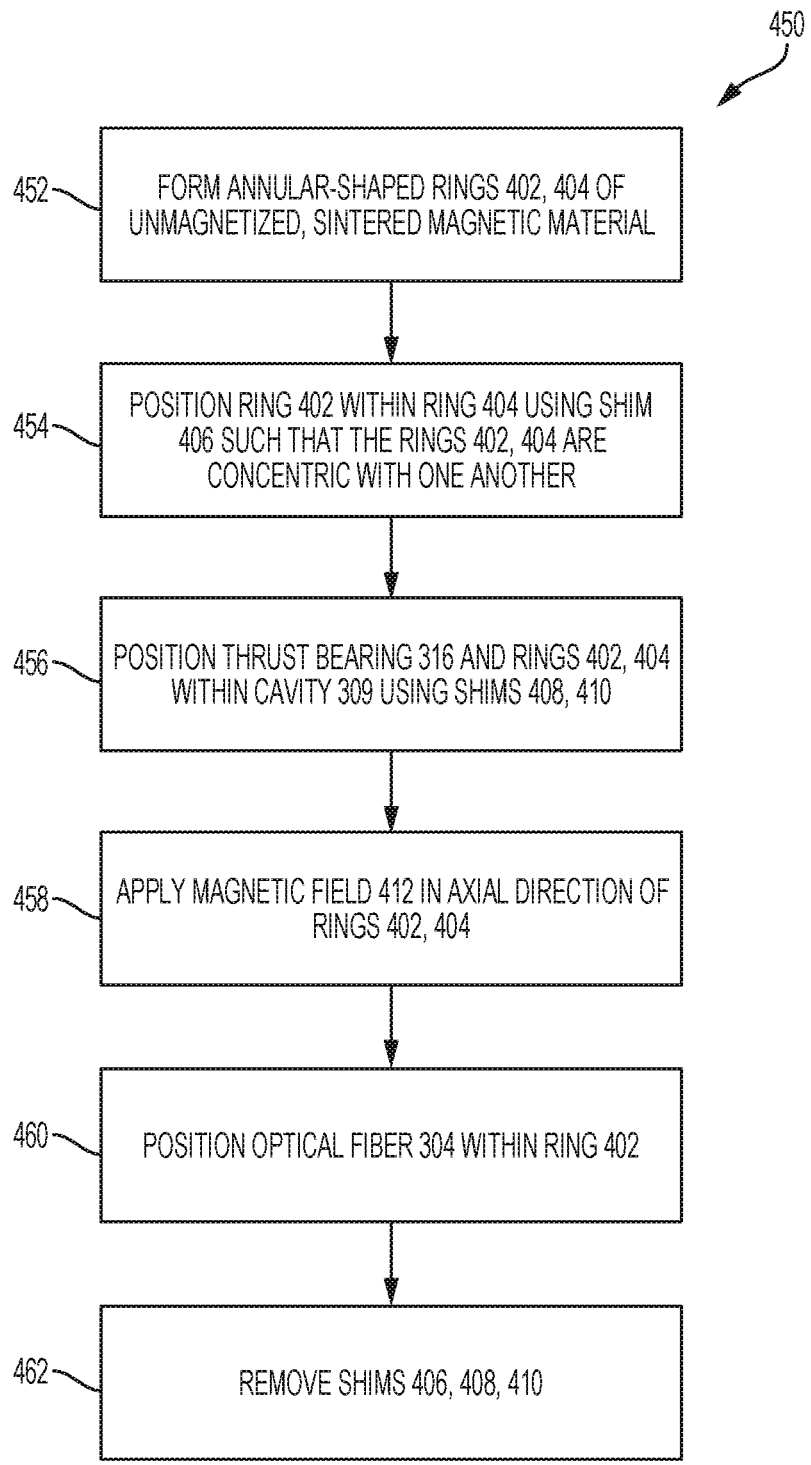

FIGS. 4A-4B are diagrams showing an example process for manufacturing an assembly that includes a radially repulsive magnetic bearing (such as the radially repulsive magnetic bearing 302 of FIGS. 3A-3B). In particular, FIG. 4A shows aspects of the example manufacturing process 450 as they relate to an assembly 400 that includes a radially repulsive magnetic bearing, while FIG. 4B is a flow diagram showing the example manufacturing process 450. In some instances, manufacturing a radially repulsive magnetic bearing, such as the radially repulsive magnetic bearing 302 of FIGS. 3A-3B, may be difficult due to the repulsive nature of the magnets. In addition, some permanent magnets may be prone to breakage. In some cases, however, the process 450 may allow for manufacture of the assembly 400 by manufacturing the radially repulsive magnetic bearing in an unmagnetized state and then magnetizing the bearing after it has been assembled.

At step 452, annular-shaped rings 402, 404 of unmagnetized, sintered magnetic material are formed. In some cases, the rings 402, 404 may be formed by placing the unmagnetized, sintered magnetic material in casings. In some embodiments, the sintered material may include NdFeB powder or another type of unmagnetized material that may become magnetic upon application of a magnetic field. The rings 402, 404 may, after a magnetic field is applied, become magnets 312, 314 of FIGS. 3A-3B. The outer radius of the ring 402 is less than the inner radius of the ring 404 so that the ring 402 may be placed within the inner radius of the ring 404 as shown in FIG. 4A.

At step 454, the ring 402 is positioned within the ring 404 such that the rings 402, 404 are concentric with one another. A non-magnetic shim 406 may be used to separate the rings 402, 404 and maintain their concentric placement, since the material is not magnetized at this time. The rings 402, 404 may be positioned such that there is an offset between the structural symmetric axis of the ring 402 and a magnetic neutral axis of the magnets formed when the material within the rings 402, 404 is magnetized. The shim 406 may be a plastic or other type of non-magnetic material. Since the rings are not magnetized at steps 452 and 454, they may be handled and positioned without fear of breaking.

At step 456, the thrust bearing 316 and the rings 402, 404 are positioned within a cavity 309 defined by the housing 308. The thrust bearing 316 may be positioned such that it is disposed at a first end of the housing 308 (the left side of the assembly 400 shown in FIG. 4A) opposite an opening defined by the housing 308 (the right side of the assembly 400 shown in FIG. 4A). In some instances, this may include coupling the outer ring 404 to a wall of the cavity 309. The outer ring 404 may be coupled using any suitable means, such as by adhesive materials (e.g., a type of glue or epoxy). The thrust bearing 316 and rings 402, 404 may be positioned using non-magnetic shims 408, 410. As shown in FIG. 4A, the shim 406 may be placed between the attachment 319 and the wall of the cavity 309, and the shim 408 may be placed between the ring 402 and a portion 317 of the housing 308. The shims 408, 410 may be a plastic or other type of non-magnetic material, and may be the same as or different from the material used for shim 406.

At step 458, a magnetic field 412 is applied to the assembly 400. The magnetic field may be relatively strong, and may be strictly orthogonal to the axis of the rings 402, 404. The magnetic field 412 may be withdrawn once the rings formed by the rings 402, 404 acquire sufficient remnant magnetism. Once magnetized, the rings 402, 404 may form a radially repulsive magnetic bearing. When the magnetic field 412 is withdrawn, the inner ring 402 (through the thrust bearing 316) will be applying a force against the portion 317 of the housing 308 due to the offset between the structural and magnetic neutral axes of the rings 402, 404, and the thrust bearing 316 may counteract this force.

At step 460, the optical fiber 304 is positioned within and coupled to the ring 402. The optical fiber 304 may be coupled to the ring 402 using any suitable means, such as adhesive materials (e.g., glue or epoxy).

At step 462, the shims 406, 408, 410 are removed. In some cases, the shims 408, 410 may be removed before the shim 406. The assembly 400 may then be mechanically and magnetically stable, creating a plug-connector carrying a "floating fiber" in the middle. The assembly may thus be ready to mate to a suitable "fixed fiber" plug (e.g., the connector 310 of FIG. 3A) that has matching dimensions and an optical fiber that is in concentric alignment with respect to its housing.

The example process of FIGS. 4A-4B may include additional or different operations, and the operations may be performed in the order shown or in another order. In some cases, one or more of the operations shown in FIGS. 4A-4B are implemented as processes that include multiple operations, sub-processes, or other types of routines. In some cases, operations can be combined, performed in another order, performed in parallel, iterated, or otherwise repeated or performed another manner. Similarly, for those designs where magnet 404 is part of the fixed fiber plug (e.g., magnet 402 being bonded onto the floating side), magnetization field 412 may be applied after the fixed and floating plugs are fastened together using fastener 311.

Figure 5:
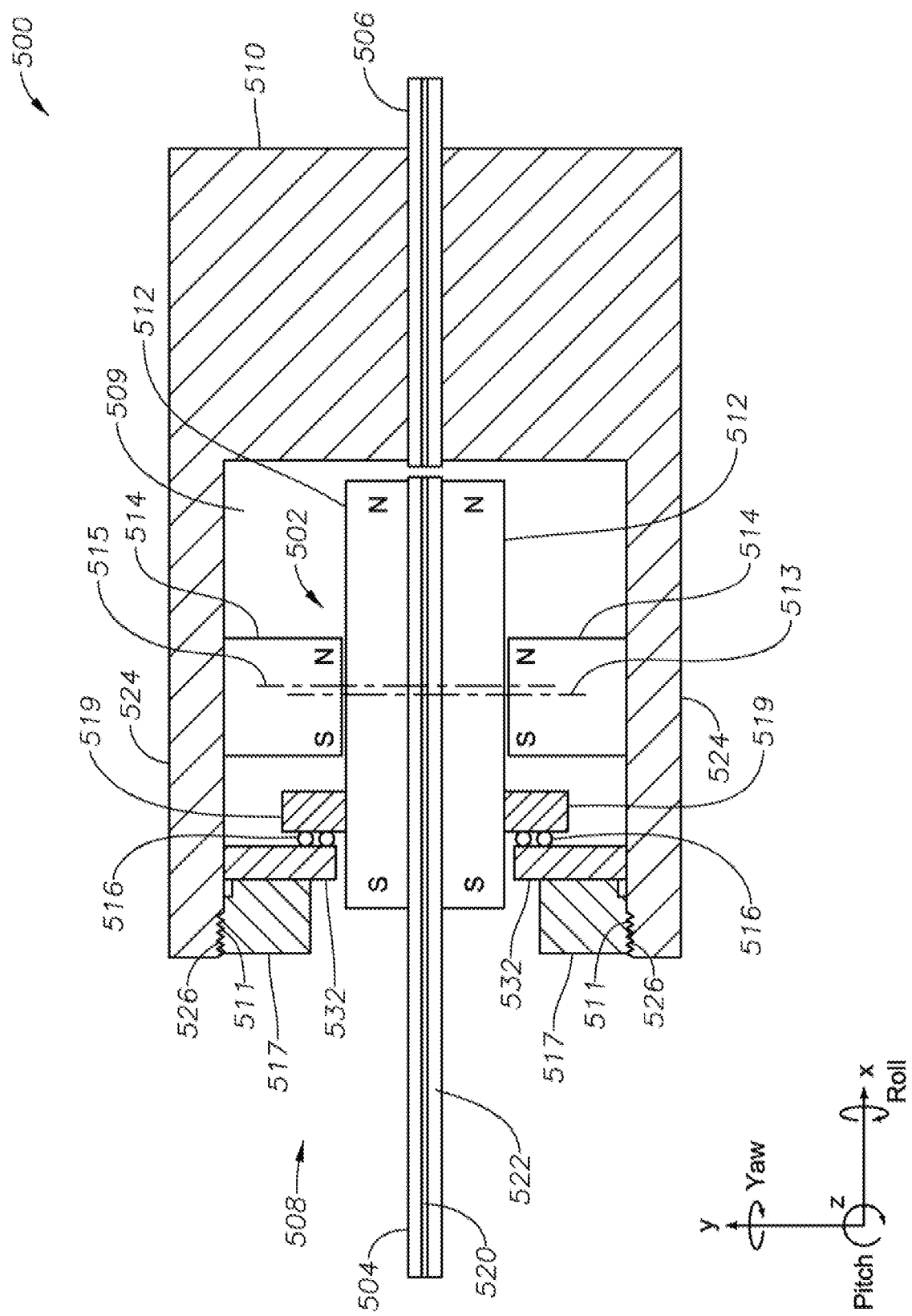
FIG. 5 is a cross-sectional view of another example system for self-aligning elements of two platforms using a radially repulsive magnetic bearing.
Figure 6:
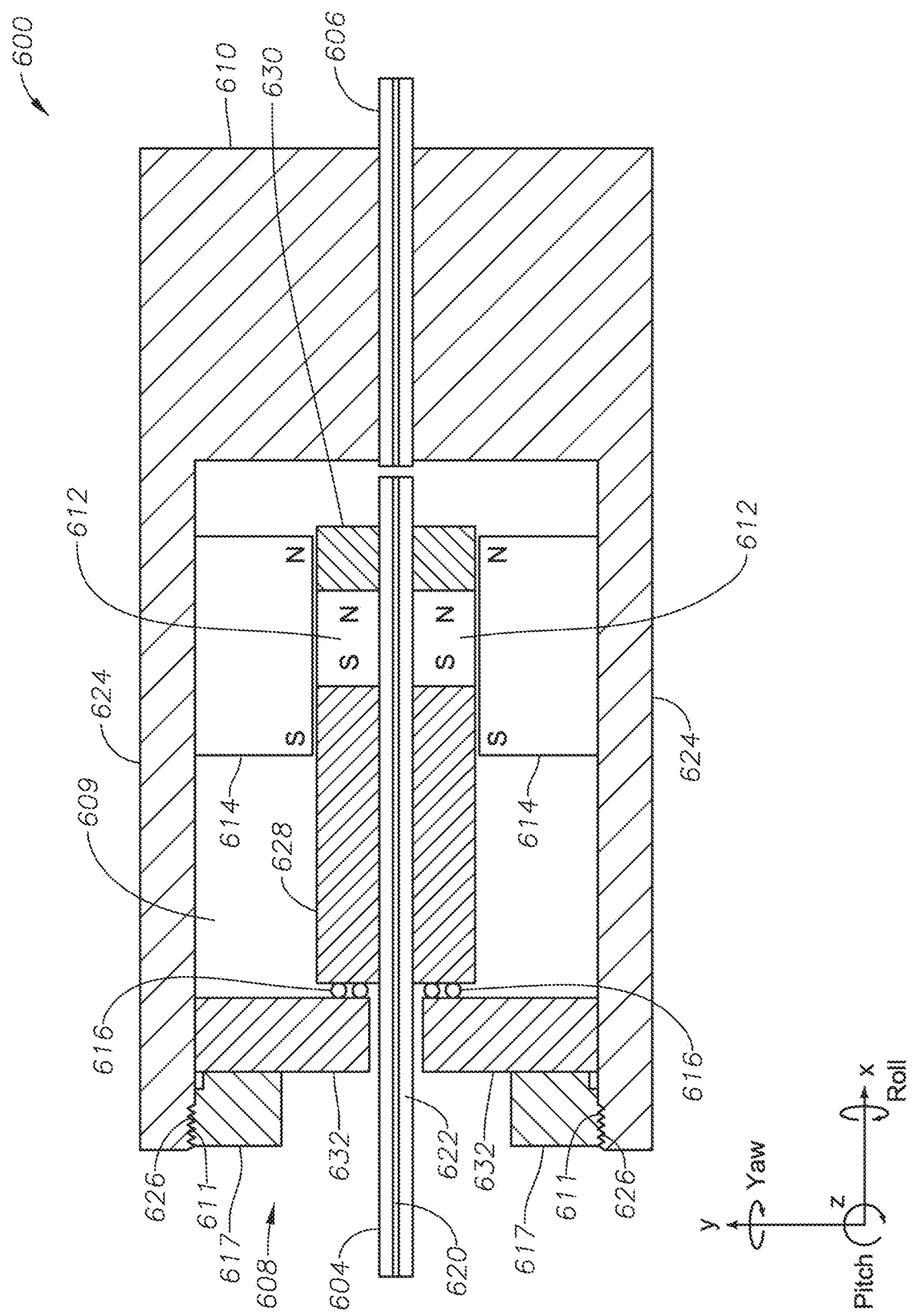
FIG. 6 is a cross-sectional view of a further example system for self-aligning elements of two platforms using a radially repulsive magnetic bearing.
Figure 7:
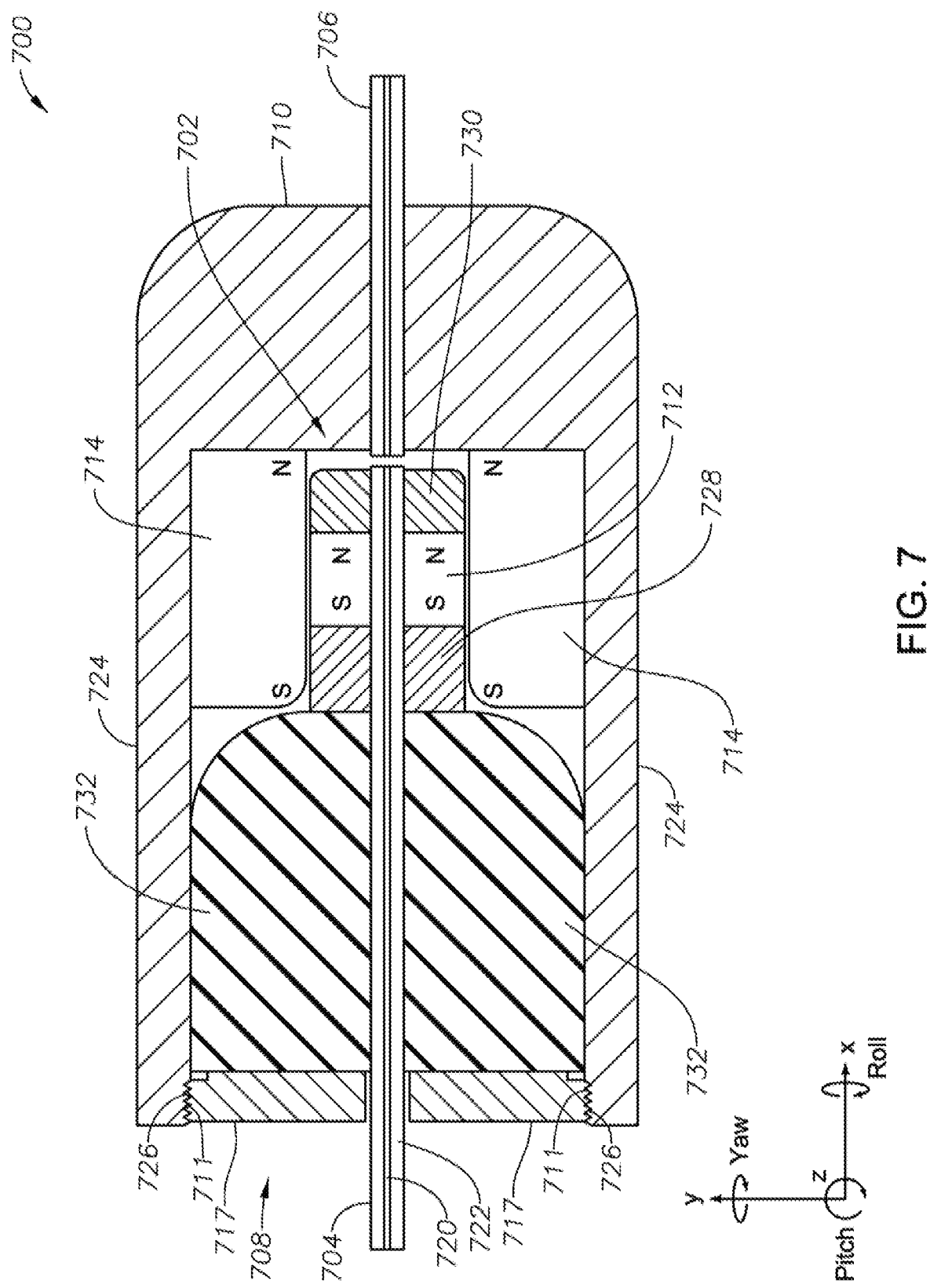
FIG. 7 is a cross-sectional view of yet another example system for self-aligning elements of two platforms using a radially repulsive magnetic bearing.

FIGS. 5-7 illustrate other example systems for self-aligning elements of two platforms using a radially repulsive magnetic bearing. Similar to system 300 shown in FIGS. 3A and 3B, the systems shown in FIGS. 5-7 use a radially repulsive magnetic bearing to self-align elements (e.g., optical elements) of two platforms. However, in system 300, the radially repulsive magnetic bearing comprises two axially polarized magnets that are mounted on one of the two platforms. In comparison, in the systems shown in FIGS. 5-7, the magnetic bearing comprises a first axially polarized magnet mounted on one of the platforms and a second axially polarized magnet mounted on the other platform.

FIG. 5 illustrates a cross-sectional view of one such system, specifically example system 500, for self-aligning elements of two platforms using radially repulsive magnetic bearings in accordance with a particular embodiment of the present invention. In general, system 500 includes a floating fiber assembly 508 (e.g., a first platform) having an optical fiber 504 and a fixed fiber assembly 510 (e.g., a second platform) having an optical fiber 506. System 500 uses a radially repulsive magnetic bearing 502 to align optical fibers 504 and 506 when the floating fiber assembly 508 and fixed fiber assembly 510 are coupled together.

As shown in FIG. 5, floating fiber assembly 508 comprises optical fiber 508, a first axially polarized magnet 512, a mounting ring 519, a thrust bearing 516, and an alignment guide 532, whereas fixed fiber assembly 510 comprises optical fiber 506, an axially polarized magnet 514, and a housing 524 that extends from the exterior of the assembly 510 and is concentric with the end of optical fiber 506. A locknut 517 serves to push, hold and/or lock the floating fiber assembly 508 into the fixed fiber assembly 510 when the two assemblies are coupled together. In particular embodiments, the locknut 517 may also be removed to decouple to the two assemblies.

In certain embodiments, optical fiber 504 and/or optical fiber 506 may each comprise a single-core fiber, a multi-core fiber, or a plurality of optical fibers. In addition, the fiber and/or fibers may include an outer sheath. In particular embodiments, the outer sheath may be a cladding that comes with the fiber or a ferrule. As shown in FIG. 5, optical fiber 504 comprises a fiber core 520 and fiber sheath 522.

Focusing on floating fiber assembly 508, first axially polarized magnet 512 is coupled to, and concentric with, the distal end of optical fiber 504. As shown in FIG. 5, the north pole of magnet 512 is located at the distal end of the magnet, while the south pole of magnet 512 is located at the proximal end. However, the opposite orientation is also acceptable provided it matches the orientation of the second axially polarized magnet 514 (i.e., the north poles are aligned with each other and the south poles are aligned with each other).

Mounting ring 519 is concentric with, and mounted on, the proximal end of magnet 512. In particular embodiments, mounting ring 519 may comprise any suitable rigid, non-magnetic material, and may have any appropriate geometry (ring-shaped or otherwise), but generally provides a structure upon which to mount thrust bearing 516, which couples first axially polarized magnet 512 to alignment guide 532. Alignment guide 532, in turn, interfaces with the interior of housing 524 on the fixed fiber assembly 510.

In the embodiment shown in FIG. 5, alignment guide 532 is a ring-shaped disc that is concentric with optical fiber 504 and coupled to the proximal side of thrust bearing 516. The radial surface of alignment guide 532 is configured to interface with the interior surface of housing 524. In this way, alignment guide 532 helps guide the insertion of first axially polarized magnet 512 into the center of second axially polarized magnet 514 (discussed in more detail below) when the floating fiber assembly 508 is coupled or mated with fixed fiber assembly 510.

When the assemblies are coupled together, alignment guide 532 is held in place by locknut 517, which is located just proximal of alignment guide 532. Accordingly, the disposition of locknut 517 indirectly controls the offset between the magnetic neutral axis 515 and the structural symmetrical axis 513 of the two magnets, as well as the operating gap between the terminal ends of optical fibers 504 and 506. As shown in FIG. 5, locknut 517 includes a threaded portion 511 that is configured to interface with a complimentary threaded portion 526 on fixed fiber assembly 510. These complementary threaded portions 511 and 526 allow the two platforms to be rigidly and removably coupled together. In particular embodiments, locknut 517 may comprise any suitable non-magnetic material and/or geometry. Furthermore, although system 500 is illustrated as including a threaded fastener (e.g., comprising threaded portions 511 and 526), in other embodiments, a bayonet mount or snap cap fitting may be used to rigidly couple floating fiber assembly 508 and fixed fiber assembly 510. With the benefit of this disclosure, one of ordinary skill in the art should be able to select other alternative fastening mechanisms for locknut 517.

By including thrust bearing 516 between mounting ring 519 and alignment guide 532, floating fiber assembly 508 is able to allow movement of the first axially polarized magnet 512 in directions orthogonal to the longitudinal axis of magnet 512. That is why optical fiber 504 may be referred to as "floating," as opposed to optical fiber 506 which may be referred to as "fixed." In particular embodiments, thrust bearing 516 may be implemented using one or more of a roller bearing, a fluid bearing, a film bearing, a flexure bearing or a magnetic bearing. In the example shown in FIG. 5, thrust bearing 516 is illustrated as a roller bearing. With the benefit of this disclosure, one of ordinary skill in the art should be able to select other alternative implementations for thrust bearing 516.

Turning to fixed fiber assembly 510, fixed fiber assembly 510 comprises optical fiber 510, an axially polarized magnet 514, and a housing 524 that extends from the exterior of the assembly 510 and is concentric with the end of second optical fiber 506. Housing 524 includes a threaded portion 526 that is configured to receive the threaded portion 511 of floating fiber assembly 508. Additionally, fixed fiber assembly 510 includes second axially polarized magnet 514, which is ring-shaped and mounted on the interior of housing 524, concentric with and spaced away from the terminal end of second optical fiber 506. Second axially polarized magnet 514 is configured to receive, and be concentric with first axially polarized magnet 512 when floating fiber assembly 508 is mated or coupled with fixed fiber assembly 510. Accordingly, floating fiber assembly 508 may be considered the male component of system 500 and fixed fiber assembly 510 may be considered the female component. As shown in FIG. 5, the north pole of second axially polarized magnet 514 is located towards the terminal end of optical fiber 506 of the magnet, while the south pole of magnet 514 is located away from the terminal end of optical fiber 506. However, the opposite orientation is also acceptable provided it matches the orientation of the first axially polarized magnet 512 (i.e., the north poles are aligned with each other and the south poles are aligned with each other).

When floating fiber assembly 508 is coupled with fixed fiber assembly 510 via threaded portions 511 and 526, a cavity 509 is formed between the two platforms, within the interior of housing 524. Within cavity 509, first axially polarized magnet 512 is received by ring-shaped second axially polarized magnet 514 such that a radial gap remains between the two magnets. In addition, first axially polarized magnet 512 is configured to be radially repulsive to second axially polarized magnet 514, such that when floating fiber assembly 508 and fixed fiber assembly 510 are coupled together, the two magnets 512 and 514 form a radially repulsive magnet bearing 502. In particular embodiments, magnets 512 and 514 may be implemented using permanent magnets, such as neodymium magnets (e.g., NdFeB magnets), electromagnets, other types of magnets, or a combination thereof. By positioning first axially polarized magnet 512 concentrically with first optical fiber 504 and positioning second axially polarized magnet 514 concentrically with second optical fiber 506, system 500 is able to use the interaction of magnets 512 and 514 in bearing 502 to suspend first axially polarized magnet 512 within ring-shaped second axially polarized magnet 514 and align optical fibers 504 and 506.

In addition, as shown in FIG. 5, the magnetic neutral axis 515 of the magnets 512 and 514 is offset from the structural symmetrical axis 513 of the first axially polarized magnet 512. The offset causes a force in tends to eject first axially polarized magnet 512 out of second axially polarized magnet 514. This force is counteracted by thrust bearing 516 and locknut 517, creating axial stability in the radially repulsive magnetic bearing 502.

In particular embodiments, thrust bearing 516 also allows limited freedom of movement of the floating fiber assembly 508 along the Y (yaw) axis and Z (pitch) axis of the fixed fiber assembly 510. This allows particular embodiments of the present invention to reduce and/or minimize the effect of contact variations (between floating fiber assembly 508 and fixed fiber assembly 510) on the alignment between optical fibers 504 and 506. For example, each coupling and decoupling operation between floating fiber assembly 508 and fixed fiber assembly 510 may cause alignment guide 532 and/or the threaded portions 511 and 526 to experience various non-repeating locking conditions (e.g., involving forces, torques, moments, contact points, boundary properties). However, because thrust bearing 516 allows for translational and rotational accommodation orthogonal to the longitudinal axis of the first axially polarized magnet 512, such variations in locking conditions may be absorbed by thrust bearing 516 rather than being transmitted to the radial gap between first axially polarized magnet 512 and second axially polarized magnet 514. Thus, the radial alignment between optical fibers 504 and 506 may be minimally affected by repeated coupling and decoupling of the two platforms.

FIG. 6 illustrates a cross-sectional view of another system, system 600, for self-aligning elements of two platforms using radially repulsive magnetic bearings in accordance with a particular embodiment of the present invention. As shown in FIG. 6, system 600 includes a floating fiber assembly 608 having an optical fiber 604 and a fixed fiber assembly 610 having an optical fiber 606. System 600 uses a radially repulsive magnetic bearing 602 formed by axially polarized magnets 612 and 614 to align optical fibers 604 and 606 when floating fiber assembly 608 and fixed fiber assembly 610 are coupled together.

In general, floating fiber assembly 608 is similar to floating fiber assembly 508 shown in FIG. 5. Floating fiber assembly 608 includes first optical fiber 604, first axially polarized magnet 612, thrust bearing 616, and alignment guide 632. However, unlike in FIG. 5, thrust bearing 616 is not mounted on a mounting ring (e.g., mounting ring 519) that is coupled to the first axially polarized magnet 612. Instead, thrust bearing 616 is mounted on an insertion guide 628 that is mounted concentrically on optical fiber 604, adjacent and proximal of first axially polarized magnet 612. In particular embodiments, floating fiber assembly 610 may also include a second insertion guide 630 that is mounted concentrically on optical fiber 604, adjacent and distal of first axially polarized magnet 612. In this way, first axially polarized magnet 612 may be sandwiched between the two insertion guides 628 and 630. Insertion guides such as guides 628 and 630 may be useful in embodiments where first axially polarized magnet 612 has an axial length shorter than that of the corresponding ring-shaped second axially polarized magnet 614 on fixed fiber assembly 610. However, as discussed above, in particular embodiments, the first axially polarized magnet may have an axial length longer, shorter, or equal to an axial length of the second axially polarized magnet. The particular dimensions of insertion guides 628 and 630 may be selected to ensure that first axially polarized magnet 612 is adequately situated along the longitudinal axis of second axially polarized magnet 614 when floating fiber assembly 608 and fixed fiber assembly 610 are coupled together. In particular embodiments, insertion guide 630 may also serve to protect the distal end of first axially polarized magnet 612 from wear and tear when being inserted into the center of second axially polarized magnet 614. In general, insertion guides 628 and 630 may comprise any suitable non-magnetic material, such as an elastomer.

Otherwise, the components of system 600 are similar to those of system 500 illustrated in FIG. 5. In addition to helping ensure that first axially polarized magnet 612 is adequately positioned within ring-shaped second axially polarized magnet 614 with the two platforms are coupled together, insertion guide 628 also serves as the structure on which thrust bearing 616 is mounted. Thrust bearing 616, in turn, couples insertion guide 628 to alignment guide 632, which is secured in place with locknut 617 when the floating fiber assembly 608 and fixed fiber assembly 610 are coupled together. In particular embodiments, locknut 617 includes a threaded portion 611 that is configured to interface with a complimentary threaded portion 626 on the fixed fiber assembly 610 and removably couple the two platforms together. Again, although system 600 is shown as including a threaded fastener (e.g., comprising threaded portions 611 and 626), in other embodiments, a bayonet mount or snap cap fitting may be used in place of a threaded faster to couple the two platforms. Similarly, although thrust bearing 616 is illustrated as a roller bearing, in particular embodiments thrust bearing 616 may be implemented using one or more of a roller bearing, a fluid bearing, a film bearing, a flexure bearing, or a magnetic bearing.

Fixed fiber assembly 610 is also similar to fixed fiber assembly 510 illustrated in FIG. 5. Generally, fixed fiber assembly 610 includes second optical fiber 606 and a ring-shaped housing 624 that extends from the exterior of assembly 610 and is concentric with the end of second optical fiber 606. Housing 624 includes a threaded portion 626 that is configured to receive the threaded portion 611 of locknut 617. Additionally, fixed fiber assembly 610 includes second axially polarized magnet 614, which is ring-shaped and mounted on the interior of housing 624, concentric with, and spaced away from the longitudinal axis of optical fiber 606. Second axially polarized magnet 614 is configured to receive, and be concentric with, first axially polarized magnet 612 when floating fiber assembly 608 is coupled with fixed fiber assembly 610.

When floating fiber assembly 608 is coupled with fixed fiber assembly 610 using locknut 617, a cavity 609 is formed between the two platforms, within the interior of housing 624. Within cavity 609, first axially polarized magnet 612 is received by ring-shaped second axially polarized magnet 614 such that a radial gap remains between the two magnets. In addition, first axially polarized magnet 612 is configured to be radially repulsive to second axially polarized magnet 614, such that when the platforms 608 and 610 are coupled together, the two magnets 612 and 614 form a radially repulsive magnet bearing 602. By positioning first axially polarized magnet 612 concentrically with first optical fiber 604 and positioning second axially polarized magnet 614 concentrically with second optical fiber 606, system 600 is able to use the interaction of magnets 612 and 614 in bearing 602 to suspend first axially polarized magnet 612 within ring-shaped second axially polarized magnet 614 and align optical fibers 604 and 606. Furthermore, using thrust bearing 616 to couple first axially polarized magnet 612 to coupling ring 617 allows the platforms 608 and 610 to be rigidly coupled together (via threaded portions 611 and 626) while still allowing for drift that may occur between system components due to thermal expansion or other stresses. Thrust bearing 616 also allows limited freedom of movement of the floating fiber assembly 608 along the Y (yaw) axis and Z (pitch) axis of the fixed fiber assembly 610. This allows particular embodiments of the present invention to reduce and/or minimize the effect of contact variations (between floating fiber assembly 608 and fixed fiber assembly 610) on the alignment between optical fibers 604 and 606.

FIG. 7 illustrates a cross-sectional view of yet another system for self-aligning elements of two platforms using radially repulsive magnetic bearings in accordance with a particular embodiment of the present invention. In particular, FIG. 7 illustrates a system 700, which is similar to the systems illustrated in FIGS. 5 and 6. However, system 700 uses an elastomeric alignment guide, rather than a ball bearing, to absorb drifts as well as misalignment forces within the system.

As shown in FIG. 7, system 700 includes a floating fiber assembly 708 comprising an optical fiber 704 and a fixed fiber assembly 710 comprising an optical fiber 706. System 700 uses a radially repulsive magnetic bearing 702 to align optical fibers 704 and 706 when assemblies 708 and 710 are coupled together.

In general, floating fiber assembly 708 includes optical fiber 708, first axially polarized magnet 712, insertion guides 728 and 730, and elastomeric alignment guide 732. In certain embodiments, optical fiber 704 and/or optical fiber 706 may each comprise a single-core fiber, a multi-core fiber, or a plurality of optical fibers. In addition, the fiber and/or fibers may include an outer sheath. In particular embodiments, the outer sheath may be a cladding that comes with the fiber or a ferrule. As shown in FIG. 7, optical fiber 704 comprises a fiber core 720 and fiber sheath 722.

First axially polarized magnet 712 is coupled to, and concentric with optical fiber 704. Also coupled concentrically on optical fiber 704, are insertion guide 728, which is adjacent and proximal to first axially polarized magnet 712, and insertion guide 730, which is adjacent and distal to first axially polarized magnet 712. In this way, first axially polarized magnet 712 may be sandwiched between the two insertion guides 728 and 730. Insertion guides such as guides 728 and 730 may be useful in embodiments where first axially polarized magnet 712 has an axial length shorter than that of the corresponding ring-shaped second axially polarized magnet 714 on fixed fiber assembly 610. The particular dimensions of insertion guides 728 and 730 may be selected to ensure that first axially polarized magnet 712 is adequately situated along the longitudinal axis of second axially polarized magnet 714 when floating fiber assembly 708 and fixed fiber assembly 710 are coupled together, especially in embodiments where first axially polarized magnet 712 has a shorter axial length than second axially polarized magnet 714. In particular embodiments, insertion guide 730 may also serve to protect the distal end of first axially polarized magnet 712 from wear and tear when being inserted into the center of second axially polarized magnet 714. In general, insertion guides 728 and 730 may comprise any suitable non-magnetic material, including but not limited to elastomers.

Also mounted on optical fiber 704, adjacent and proximal of insertion guide 728 is elastomeric alignment guide 732. Like in the alignment guides 532 (FIG. 5) and 632 (FIG. 6), the radial surface of elastomeric alignment guide 732 interfaces with the interior surface of housing 724 and helps facilitate the insertion of first axially polarized magnet 712 into the center of second axially polarized magnet 714. However, elastomeric alignment guide 732 is also configured to accommodate for drift among the system components (e.g., due to thermal expansion, structure changes) that is orthogonal to and/or along the longitudinal axis of optical fiber 704 thereby behaving as a flexure bearing. In particular embodiments, elastomeric alignment guide 732 may comprise any suitable elastomer and any suitable geometry so long as the chosen elastomeric material and geometry provide adequate leeway to accommodate drift by the components of the system. For example, as shown in FIG. 7, elastomeric alignment guide 732 is generally bell-shaped illustrated as being bell-shaped; however, other geometries are possible within the teachings of the present invention.

When first axially polarized magnet 712 is inserted into second axially polarized magnet 714, elastomeric alignment guide 732 is secured in place by locknut 717, which includes a threaded portion 711 that is configured to interface with a complimentary threaded portion 726 on fixed fiber assembly 710 and removably couple the two platforms together. Again, although system 700 is shown as including a threaded fastener (e.g., comprising threaded portions 711 and 726), in other embodiments, a bayonet mount or snap cap fitting may be used in place of a threaded faster to couple the two platforms.

System 700 also includes fixed fiber assembly 710, which is similar to fixed fiber assemblies 510 (FIG. 5) and 610 (FIG. 6) described above. Generally, fixed fiber assembly 710 includes second optical fiber 706 and a ring-shaped housing 724 that extends from the exterior of assembly 710 and is concentric with the end of second optical fiber 706. Housing 724 includes a threaded portion 726 that is configured to receive the threaded portion 711 of locknut 717. Additionally, fixed fiber assembly 710 includes second axially polarized magnet 714, which is ring-shaped and mounted on the interior of housing 724, concentric with the longitudinal axis of second optical fiber 706. Second axially polarized magnet 714 is configured to receive, and be concentric with, first axially polarized magnet 712 when floating fiber assembly 708 is coupled with fixed fiber assembly 710, such that a radial gap remains between the two magnets. In addition, first axially polarized magnet 712 is configured to be radially repulsive to second axially polarized magnet 714, such that when the assemblies 708 and 710 are coupled together, the two magnets 712 and 714 form a radially repulsive magnet bearing 702. By positioning first axially polarized magnet 712 concentrically with first optical fiber 704 and positioning second axially polarized magnet 714 concentrically with second optical fiber 706, system 700 is able to use the interaction of magnets 712 and 714 in bearing 702 to suspend first axially polarized magnet 712 within ring-shaped second axially polarized magnet 714 and align optical fibers 704 and 706. At the same time, elastomeric alignment guide 723 allows the two platforms to be rigidly connected (via locknut 717) while allowing for drift that may occasionally occur between the components of the system (e.g., due to thermal expansion). Elastomeric alignment guide 732 also allows limited freedom of movement of the floating fiber assembly 708 along the Y (yaw) axis and Z (pitch) axis of the fixed fiber assembly 710. This allows particular embodiments of the present invention to reduce and/or minimize the effect of contact variations (between floating fiber assembly 708 and fixed fiber assembly 710) on the alignment between optical fibers 704 and 706.

Embodiments of the present disclosure provide systems and methods for self-aligning elements of two coupled platforms that may overcome limitations of conventional systems and methods. It will be appreciated that above-disclosed and other features and functions, or alternatives thereof, may be desirably combined into many other different systems or applications in accordance with the disclosure. It will also be appreciated that various presently unforeseen or unanticipated alternatives, modifications, variations, or improvements therein may be subsequently made by those skilled in the art which alternatives, variations and improvements are also intended to be encompassed by the following claims.

What is claimed is:

1. An ophthalmic surgical system comprising:
a laser source configured to generate optical pulses and direct the optical pulses along an optical path defined by one or more optical elements; and
a housing configured to be coupled to a handpiece, the housing comprising a radially repulsive magnetic bearing that comprises:
a first axially polarized magnet coupled to an optical element defining the optical path;
a second axially polarized magnet concentric with and radially repulsive to the first axially polarized magnet, the second axially polarized magnet coupled to the housing; and
a thrust bearing coupled to the housing and the first axially polarized magnet, wherein the thrust bearing is configured to allow movement of the optical element coupled to the first axially polarized magnet in a direction orthogonal to the axial direction, and to counteract a magnetic force caused by the offset,
wherein the radially repulsive magnetic bearing is configured, when the housing is coupled to the handpiece, to optically align an optical element of the handpiece with the optical element coupled to the first axially polarized magnet.

2. The ophthalmic surgical system of claim 1, wherein a magnetic neutral axis of the first and second axially polarized magnet is offset from a structural symmetrical axis of the first axially polarized magnet.

3. The ophthalmic surgical system of claim 1, wherein an axial length of the first axially polarized magnet is not equal to an axial length of the second axially polarized magnet.

4. The ophthalmic surgical system of claim 1, wherein the thrust bearing includes one or more of a roller bearing, a fluid bearing, a film bearing, a flexure bearing, and a magnetic bearing.

5. The ophthalmic surgical system of claim 1, wherein the housing defines a cavity and an opening at a first end, the housing is configured to couple to the handpiece at the first end, the second axially polarized magnet is coupled to a wall of the cavity, and first axially polarized magnet is coupled to the housing via the thrust bearing at a second end of the housing opposite the first end.

6. The ophthalmic surgical system of claim 1, wherein the housing further comprises a fastener for coupling to the handpiece, and a gap between the optical element coupled to the first axially polarized magnet and the optical element in the handpiece is defined at least in part by the thrust bearing and the fastener.

7. The ophthalmic surgical system of claim 1, wherein the one or more optical elements that define the optical path include one or more of an optical fiber, a lens, a mirror, a prism, and a diffraction grating.

* * * * *